United States Patent
Salys et al.

(10) Patent No.: US 7,433,739 B1
(45) Date of Patent: Oct. 7, 2008

(54) PASSIVE FIXATION MECHANISM FOR EPICARDIAL SENSING AND STIMULATION LEAD PLACED THROUGH PERICARDIAL ACCESS

(75) Inventors: Scott Salys, Los Angeles, CA (US);
Chris Parrillo, Simi Valley, CA (US);
Matt Phillips, Sylmar, CA (US); Luz Padilla, Pacoima, CA (US); Jnyan Patel, Woodland Hills, CA (US); Kevin L. Morgan, Simi Valley, CA (US);
Michael Yang, Thousand Oaks, CA (US); Sheldon Williams, Green Valley, CA (US); Andrew W. McGarvey, Minneapolis, MN (US)

(73) Assignee: Pacesetter, Inc., Sylmar, CA (US)

( * ) Notice: Subject to any disclaimer, the term of this patent is extended or adjusted under 35 U.S.C. 154(b) by 406 days.

(21) Appl. No.: 11/001,374

(22) Filed: Nov. 30, 2004

(51) Int. Cl.
*A61N 1/05* (2006.01)

(52) U.S. Cl. .................... 607/115; 607/119

(58) Field of Classification Search ............. 607/115, 607/116, 119, 122, 123, 125, 126; 600/372, 600/373, 374, 377, 381
See application file for complete search history.

(56) References Cited

U.S. PATENT DOCUMENTS

| | | | | |
|---|---|---|---|---|
| 4,142,530 A | * | 3/1979 | Wittkampf | 607/116 |
| 4,235,246 A | | 11/1980 | Weiss | 128/785 |
| 4,299,239 A | | 11/1981 | Weiss et al. | 128/785 |
| 4,620,550 A | | 11/1986 | Doroshuk | 128/785 |
| 4,865,037 A | | 9/1989 | Chin et al. | 128/419 D |
| 4,971,070 A | * | 11/1990 | Holleman et al. | 607/129 |
| 4,991,578 A | | 2/1991 | Cohen | 128/419 D |
| 5,217,028 A | | 6/1993 | Dutcher et al. | 128/785 |
| 5,387,233 A | | 2/1995 | Alferness et al. | 607/126 |
| 5,391,200 A | * | 2/1995 | KenKnight et al. | 607/129 |
| 5,397,343 A | * | 3/1995 | Smits | 607/130 |
| 5,653,734 A | | 8/1997 | Alt | 607/5 |
| 5,749,922 A | * | 5/1998 | Slepian et al. | 29/469.5 |
| 5,807,306 A | * | 9/1998 | Shapland et al. | 604/21 |
| 5,871,532 A | | 2/1999 | Schroeppel | 607/128 |
| 5,876,430 A | * | 3/1999 | Shoberg et al. | 607/122 |
| 5,928,260 A | * | 7/1999 | Chin et al. | 606/200 |
| 6,206,912 B1 | * | 3/2001 | Goldsteen et al. | 623/1.23 |
| 6,212,434 B1 | * | 4/2001 | Scheiner et al. | 607/123 |
| 6,406,420 B1 | * | 6/2002 | McCarthy et al. | 600/16 |

(Continued)

FOREIGN PATENT DOCUMENTS

WO    WO 2004/011081 A1    2/2004

OTHER PUBLICATIONS

Andre D'Avila, M.D., et al. *"Pericardial Anatomy for the Inteventional Electrophysiologist,"* J Cardiovasc Electrophysiol, Apr. 2003; vol. 14, No. 4, pp. 422-430.

(Continued)

*Primary Examiner*—Carl H. Layno
*Assistant Examiner*—Jon-Eric C. Morales (57) ABSTRACT

An implantable lead having an elongated lead body that includes an electrical conductor extending between a distal end of the lead body and a proximal end of the lead body is disclosed. The lead further includes an electrode formed at the distal end of the lead body, the electrode being coupled to the electrical conductor and one or more passive fixation mesh sections coupled to the distal end of the lead body that promotes tissue over growth.

30 Claims, 7 Drawing Sheets

U.S. PATENT DOCUMENTS

| | | | |
|---|---|---|---|
| 6,505,082 B1 * | 1/2003 | Scheiner et al. | 607/123 |
| 6,584,362 B1 * | 6/2003 | Scheiner et al. | 607/122 |
| 6,687,549 B1 | 2/2004 | Helland et al. | 607/122 |
| 6,718,212 B2 | 4/2004 | Parry et al. | 607/130 |
| 2002/0045855 A1 * | 4/2002 | Frassica | 604/109 |
| 2003/0040787 A1 * | 2/2003 | Flynn et al. | 607/122 |
| 2003/0114908 A1 | 6/2003 | Flach | 607/129 |
| 2004/0019377 A1 * | 1/2004 | Taylor et al. | 623/2.11 |
| 2004/0127967 A1 | 7/2004 | Osypka | 607/122 |

OTHER PUBLICATIONS

NonFinal Office Action, mailed Mar. 12, 2007: Related U.S. Appl. No. 11/121,881.

Final Office Action, mailed Jul. 12, 2007: Related U.S. Appl. No. 11/121,881.

Notice of Allowance, mailed Sep. 13, 2007: Related U.S. Appl. No. 11/121,881.

Final Office Action, mailed Apr. 29, 2008: Related U.S. appl. No. 11/001,375.

Kint, Darwin et al, "A review on the potentially biodegradability of poly(ethylene terephthalate)" Polym Int 1999;48:346-352.

Restriction Requirement, mailed Sep. 25, 2007: Related U.S. Appl. No. 11/001,375.

NonFinal Office Action, mailed Oct. 22, 2007: Related U.S. Appl. No. 11/001,375.

* cited by examiner

PASSIVE FIXATION MECHANISM FOR EPICARDIAL SENSING AND STIMULATION LEAD PLACED THROUGH PERICARDIAL ACCESS

CROSS-REFERENCE TO RELATED APPLICATIONS

This application is related to copending U.S. patent application Ser. No. 11/001,375, titled "Epicardial Cardiac Sensing and Pacing Lead Placed Through Pericardial Access", filed Nov. 30, 2004 concurrently herewith.

FIELD OF THE INVENTION

The invention generally relates to passive fixation leads and more particularly relates to epicardial sensing and stimulation leads.

BACKGROUND

Implantable electrical stimulation devices are now commonly used in medical practice. These devices provide periodic electrical stimulus, i.e., therapeutic pulses or shocks, to the heart or other organs to regulate the function of the stimulated organ. Implantable devices therefore, commonly employ leads for coupling an electrical pulse generator to excitable organ tissue.

Historically, the leads of a dual-chamber pacemaker, for example, are inserted transvenously within the right side of the heart. Under several circumstances, however, simultaneous pacing of both the right and the left sides of the heart may be desirable. For example, pacing both ventricles simultaneously may improve the clinical status and ventricular function of patients with congestive heart failure.

In these instances a transvenous endocardial lead, typically inserted through the coronary sinus and into one of the branches of the coronary venous system, is used to deliver pacing pulses or therapeutic shock to the left ventricle. Clinically, transvenous implantation is less invasive with reduced post-operative pain and associated trauma than other common lead implantation techniques.

However, in some patients, particularly children and patients with compromised coronary sinus veins, an external or epicardial lead may be medically indicated. The implantation of an external or epicardial lead historically required a mini thoracotomy or full sternotomy surgical procedure. Thoracic surgery, which typically involves the opening of the chest cavity to expose the patient's heart, is highly traumatic to the patient. The trauma associated with thoracic surgery may be especially severe for those patients with congestive heart failure and typically also necessitates considerable in-hospital recovery time for the patient.

However, the advent of thoracoscopy in cardiac surgery allows surgeons to implant epicardial leads percutaneously into the pericardial space. In these procedures, an epicardial lead is inserted into the pericardial space through a small opening in the chest cavity and a small incision or puncture in the pericardial sac.

In the past, epicardial leads were often sutured directly to the heart wall to secure the lead in place, increasing the complexity of the implant procedure. In addition, a larger introducer may be necessary to implant a lead having a suture pad into the pericardial space, resulting in a larger incision, more scarring, and potentially more post-operative pain for the patient.

SUMMARY

In accordance with one aspect of the present invention, an implantable lead system includes an elongated lead body having an electrical conductor extending between a distal end of the lead body and a proximal end of the lead body. In this aspect of the present invention the lead system further includes an electrode formed at the distal end of the lead body, the electrode being coupled to the electrical conductor and one or more passive fixation mesh sections coupled to the distal end of the lead body that promote tissue over growth for lead fixation and stability.

BRIEF DESCRIPTION OF THE DRAWINGS

Further features and advantages may be more readily understood by reference to the following description taken in conjunction with the accompanying drawings, in which.

DETAILED DESCRIPTION

The invention is described below, with reference to detailed illustrative embodiments. It will be apparent that the invention may be embodied in a wide variety of forms, some of which may be quite different from the disclosed embodiments. For example, the invention may be implemented in unipolar, bipolar or multi-polar, epicardial, cardiac pacing and/or sensing leads having one or more pace/sense electrode(s) or sense electrode(s), respectively, at or adjacent the distal lead end of the lead.

Further, the invention may also be implemented in epicardial cardiac defibrillation/cardioversion leads having at least one cardioversion/defibrillation electrode and optionally including one or more pace/sense electrode(s) at or adjacent the distal lead end. Moreover, other sensors for sensing a physiologic parameter may be incorporated into the lead body.

Each such pace/sense electrode, sense electrode, cardioversion/defibrillation electrode and sensor is coupled with an insulated electrical conductor extending proximally through the lead body to a proximal lead end connector assembly. Consequently, the specific structural and functional details disclosed herein are merely representative and do not limit the scope of the invention. In the description that follows, like numerals or reference designators will be used to refer to like parts or elements throughout.

Figure 1:
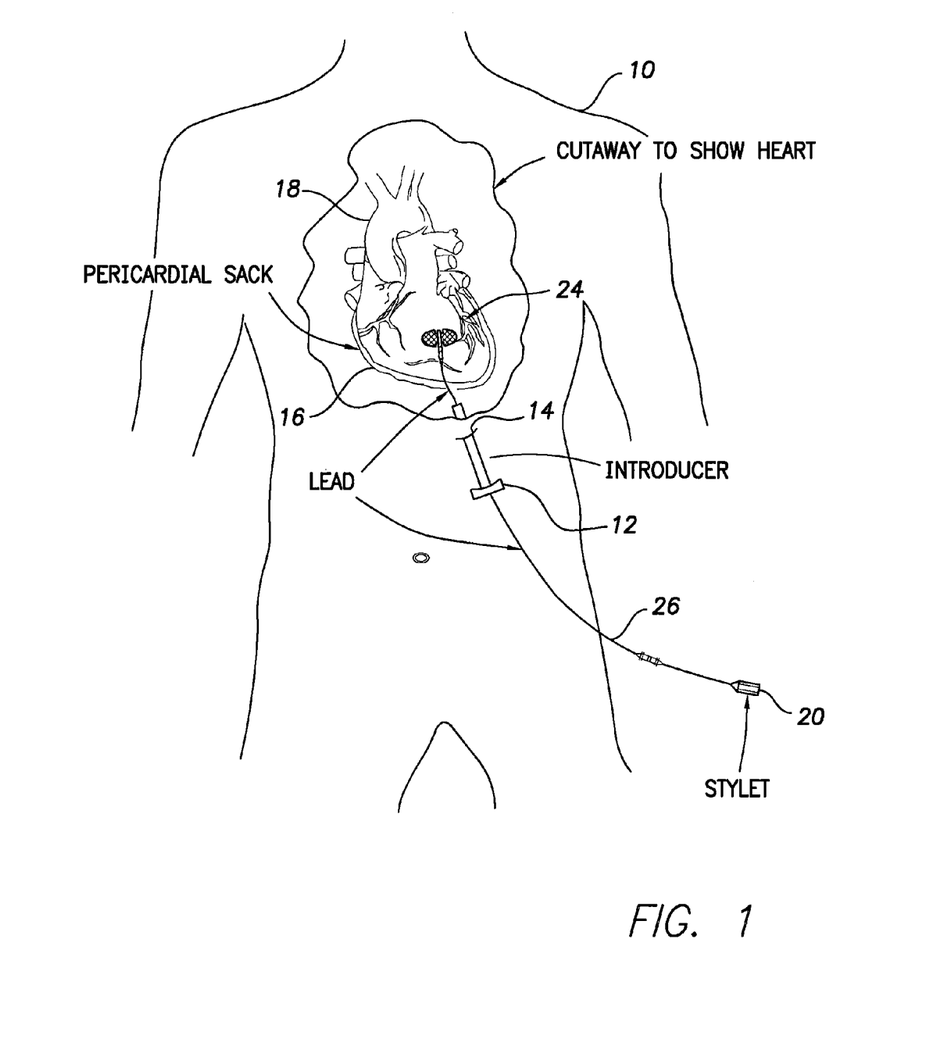
FIG. 1 is a schematic illustration of an implantable epicardial lead coupled with a patient's heart for delivering stimulation and shock therapy in accordance with one embodiment of the invention.

Several common approaches have been developed to place electrodes within the pericardial sac of the heart. For example, FIG. 1 illustrates schematically a patient's upper chest region 10 having one or more intercostal or subxyphoid incisions 14 for receiving various instruments of an epicardial implantation system in accordance with the present invention. Although FIG. 1 illustrates one incision, it will be evident that two or more incisions may also be employed. In addition, the precise locations and sizes of the incisions and the instruments used may vary depending upon the patient's anatomy and the surgeon's preferences. Each incision may accommodate a trocar (not shown) for facilitating the insertion and manipulation of one of the instruments.

According to one approach, the lead may be inserted, using a puncture needle and an associated introducing catheter or dilator. In this approach, a puncture needle having a center lumen (not explicitly shown) is inserted into the upper chest region 10 via a subxiphoid or intercostal approach and introduced into the pericardial space. The needle is guided through the pericardial space using fluoroscopic or X-ray imaging and small amounts of contrast media. Alternatively, endoscopy or ultrasound can also be used for visualization during the implant procedure. Once successful entry into the pericardial space is documented, a guidewire is inserted into the needle and advanced into the pericardial space.

In one embodiment an introducer with a dilator is then advanced over the guidewire and into the space to expand the passageway through the puncture site. The dilator may then be removed and the guidewire may be removed or left within the introducer for placing the lead into the pericardial space according to the physician's preference. An exemplary method for accessing the pericardial space is disclosed in an article entitled "Pericardial Anatomy for the Interventional Electrophysiologist", by Dr. Andre D'Avilla et al., appearing in the *J Cardiovasc Electrophysiol*, Vol. 14, pp. 422-430, April 2003, the content of which is incorporated herein by reference as if disclosed in full.

Alternatively, the pericardial sac may be perforated or excised with an endoscopic type cutting instrument introduced through a second trocar. An interior dilator may then be used to expand the passageway through the puncture site into the pericardial sac.

In one embodiment a stylet or guidewire 20 is used to steer and position a distal end 24 of the epicardial lead 26 through the interior introducer into the pericardial sac and orient an electrode against exposed epicardium tissue. Alternatively, a guide catheter may be inserted into the body over a guide wire, and an interior dilator into the pericardial sac. The epicardial lead is then fed through the inner lumen of the catheter such that the lead electrode(s) are positioned at predetermined locations. The guide catheter in this implantation technique is then withdrawn.

Capture testing may then be performed to determine if the stimulated chamber (e.g. left or right atrium or ventricle) is captured at an acceptable pacing pulse energy level at the implanted electrode location. The electrode is then passively fixated in place at a location that provides acceptable capture thresholds and reliable detection of cardiac signals that traverse the targeted chamber of the heart.

The lead body is then routed subcutaneously to locate the lead body proximal end at the site of an implanted electrical stimulation device to be attached with the implanted stimulation device in a manner well known in the art. The same procedure may be employed to implant a plurality of epicardial leads with epicardial pace/sense electrode(s) located at a plurality of sites of the epicardium of the left and right heart.

One of skill in the art will appreciate that the epicardial lead may also be implanted using a mini thoracotomy or full sternotomy surgical procedure. However, thoracoscopic procedures reduce the risks of bleeding, infection, cardiac perforation, pneumothorax, and coronary lacerations.

Figure 2:
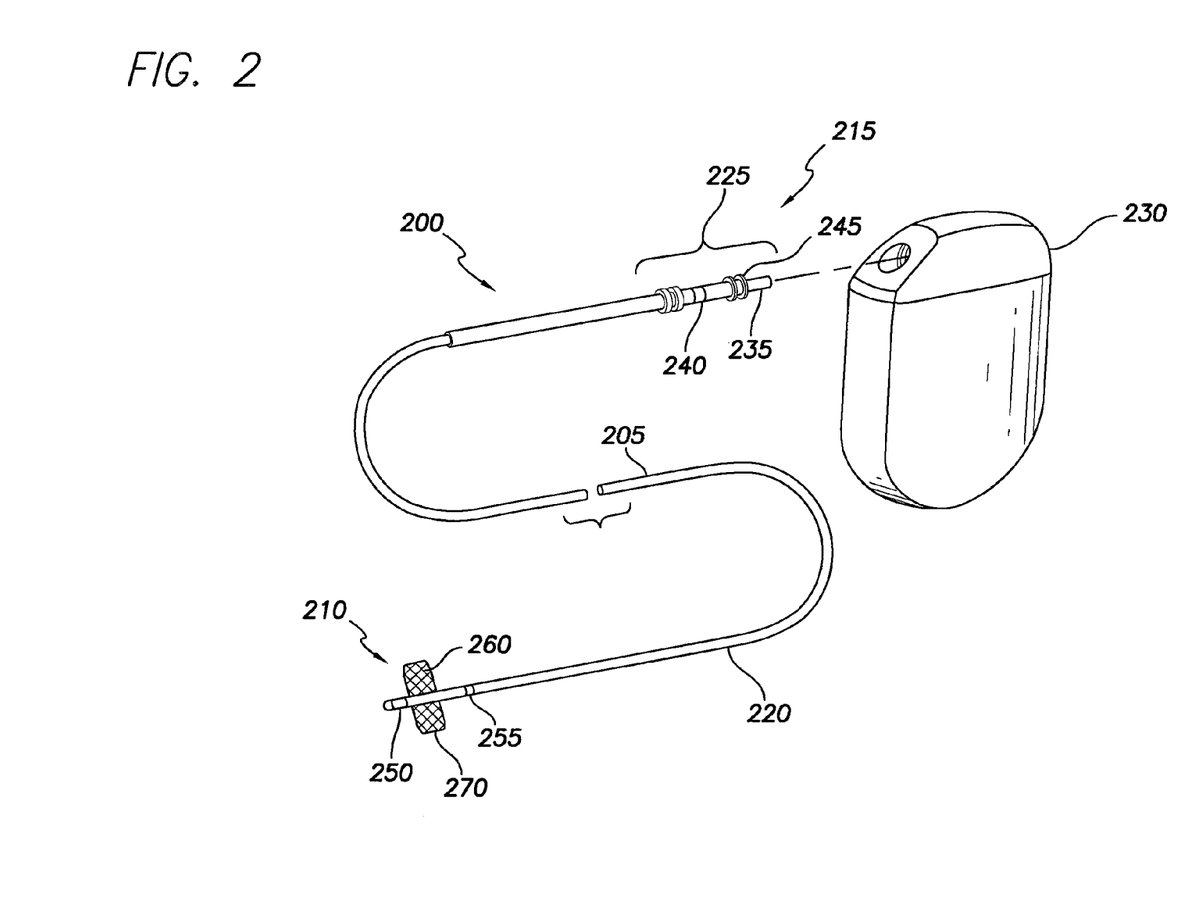
FIG. 2 is a perspective view of the implantable epicardial lead of FIG. 1 including a passive fixation mechanism coupled to the distal end of the lead body and proximal connector for electrical connection to an implantable electrical stimulation device in accordance with one embodiment of the invention.

FIG. 2 illustrates a bipolar epicardial lead 200 adapted for percutaneous subxiphoid pericardial implantation into the pericardial space of a patient's heart. The epicardial lead 200 includes a lead body 205 extending along a central longitudinal axis and including one or more mutually insulated electrical conductors (not explicitly shown) extending between a distal end 210 and a proximal end 215 of the lead body. The lead body further comprises a tubular insulating sheath 220 that overlies the electrical conductors. The tubular insulating sheath is typically made of an insulating, biocompatible material such as, by way of example, silicone rubber or polyurethane.

The proximal end 215 of the lead body includes a connector assembly 225 for mechanically and electrically coupling the lead body to an implantable stimulation device 230 such as a cardiac pacemaker or implantable cardioverter/defibrillator. In one embodiment the connector assembly 225 may conform to the IS-1 or any other industry connector assembly standard.

For example, the connector assembly in one embodiment includes, coaxial terminal contacts in the form of a pin terminal contact 235 and a ring terminal contact 240 positioned to engage corresponding electrical terminals (not explicitly shown) within a receptacle of the implantable stimulation device 230. In addition, the connector assembly includes, by way of example, spaced-apart sets of seals 245 to prevent ingress of body fluids into the receptacle of the implantable stimulation device 230.

Figure 3:
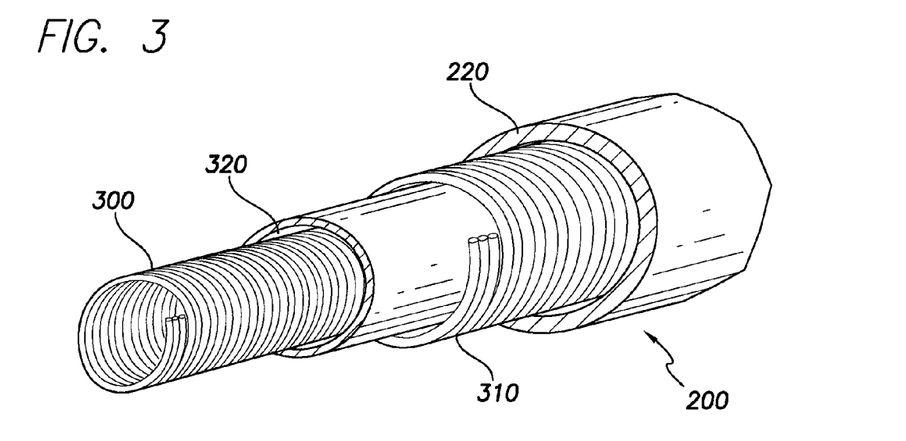
FIG. 3 is a perspective view, partially cut away and shown in section, of one construction of the implantable epicardial lead of FIG. 1 in accordance with one embodiment of the present invention.

In one embodiment the distal end 210 of the lead body 205 includes at least one electrode configured to perform at least one of sensing, pacing, cardioversion, and defibrillation of the heart. For example, in the illustrated embodiment the lead includes, by way of example, a distal electrode 250 that is mechanically and electrically coupled to a coil conductor 300 enclosed within the insulating tubular sheath as illustrated in FIG. 3. The coil conductor 300 is in turn coupled to the electrical pin contact 235 on the connector assembly 225 at the proximal end 215 of the lead.

In the illustrated embodiment, a proximal ring electrode 255 is proximally spaced from the distal electrode 250 and is suitably coupled to a second outer conductor 310 (see FIG. 3) which is coupled to the ring terminal contact 240 of the connector assembly 225. An inner insulating sheath 320, typically of silicone rubber, insulates the inner conductor coil 300 from the outer conductor coil 310 and the outer insulating sheath 220 which may similarly be of silicone rubber insulates the outer conductor coil 310 from any external grounding agents.

Figure 4:
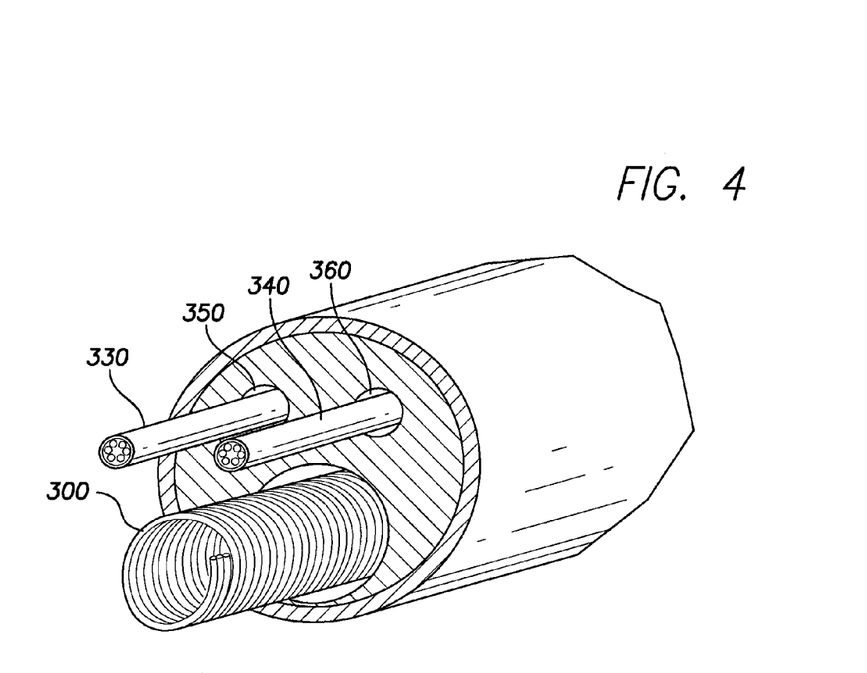
FIG. 4 is a perspective view, partially cut away and shown in section, of a second construction of the implantable epicardial lead of FIG. 1 in accordance with one embodiment of the present invention.

Alternatively, the proximal electrode 255 may be coupled to redundant conductive cables 330 and 340 that are received in lumina 350, 360 (see FIG. 4) within the lead body, which are then coupled to the ring terminal contact 240 of the connector assembly 225.

Further, in accordance with well known implantation techniques, a stylet or guidewire for delivering and steering the distal end 210 of the lead body during placement thereof may be inserted through a lumen in the connector pin terminal contact 235 and into a longitudinal passageway within the lead body. In one embodiment the passageway comprises, by way of example, the lumen of the inner conductor coil 300 that couples the contact pin 235 with, by way of example, the distal electrode 250.

Although the epicardial lead of FIG. 2 is depicted as a bipolar lead, one of skill in the art will appreciate that the invention may be practiced in a unipolar lead employing only the distal electrode 250 or as a multi-polar lead. One of skill in the art will further appreciate that the lead body 205 may further include a cardioverting-defibrillating electrode (not explicitly shown), which in one embodiment is in the form of an elongated conductive coil or in the form of a conductive polymer electrode.

In one embodiment the distal electrode 250 and the proximal electrode 255 are substantially cylindrical in shape and provide stimulation in all directions away from the lead body. However, one of skill in the art will appreciate that the distal electrode 250 and proximal electrode 255 may be formed in many shapes, e.g., a full ring shape or as a ring segment shape and still be considered to be within the scope of the invention.

In addition, in one embodiment of the present invention a surface of the distal electrode 250 (i.e. the cathode in this embodiment) may be coated, in part, with a suitable non-conductive coating such as, for example, silicone rubber, polyurethane, parylene, or a similar type coating or paint. The non-conductive coating applied to the distal electrode 250, renders the coated surface non-conductive. This has the effect of directing electrical stimulation signals through the non-coated surface of the electrode toward a targeted stimulation area. It should be understood that the amount of coating and the electrode area covered by the coating may be varied to provide a desired stimulation.

The epicardial lead, in accordance with one embodiment of the present invention includes a passive fixation mechanism 260 coupled to the distal end 210 of the lead body 205 as illustrated in FIG. 2. In this embodiment the passive fixation mechanism 260 is deployed after the distal end of the epicardial lead has been inserted into the pericardial sac to maintain the electrodes 250 and 255 in contact with the epicardium.

In one embodiment of the present invention the passive fixation mechanism comprises one or more sections of a polymer mesh coupled with the outer peripheral surface of the tubular insulating sheath 220. The passive fixation mechanism 260 encourages tissue over growth into the mesh sections to fixate and stabilize the lead in the desired location within the pericardial sac.

In one embodiment, the one or more polymer mesh sections are made of a polyester polymer with an open weave mesh. The one or more mesh sections in this embodiment are adhesively bonded to the lead body such that tissue over growth takes place while the lead is in contact with myocardium, resulting in stable fixation of the lead. In one embodiment of the invention, an enhancing silicone (or an alternative material) ring 270 may be included around the edges of the mesh sections to provide increased mechanical stability. The silicone ring 270 also promotes the full extension of the mesh sections fully when inserted into the pericardial space to ensure proper coupling of the distal electrode(s) to the heart's surface. In one embodiment, the enhancing silicone may also contain a material that gives it visibility under fluoroscopy or X-ray.

The polymer mesh sections of the passive fixation mechanism have a large enough surface area to induce a sufficient degree of tissue over growth to provide stable fixation of the lead. However, the mesh sections are also preferably small enough to be inserted through an introducer placed into the pericardial space without causing difficulty. In one embodiment of the present invention the passive fixation mechanism 260 comprises two opposing mesh sections that are oriented in a substantially symmetrical manner about the lead body. The mesh sections in this embodiment are located between the distal electrode 250 and the proximal ring electrode 255. The mesh sections have, by way of example, a surface area of approximately one square centimeter (1 $cm^2$) and may be implanted with a number fourteen French introducer.

One of skill in the art will appreciate however, that the size of the mesh sections may be varied to provide more or less stability. In addition, the thickness of the mesh and variations of the weave structure (looser or tighter weave) may also be used to achieve desired fixation results. Generally, the stability of the lead increases with increasing surface area of the mesh sections. Therefore, the surface area of the mesh sections may be varied in accordance with doctor preference, the size and functional capacity of the patient's heart, activity level of the patient, etc.

Figure 5:
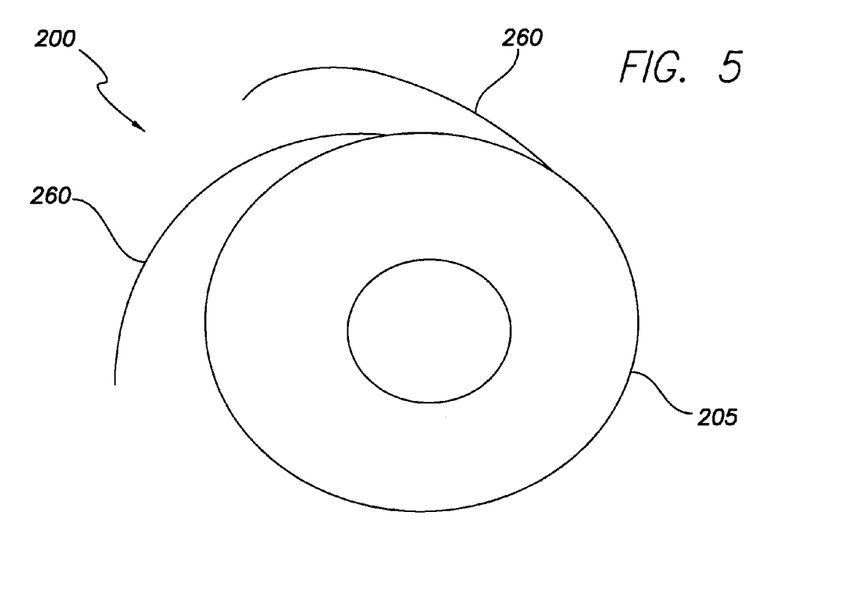
FIG. 5 is a cross section of the implantable epicardial lead of FIG. 1 having two passive fixation mesh sections coupled to opposing sides of a longitudinal axis of the lead body in accordance with one embodiment of the present invention.

However, as seen in FIG. 5, the passive fixation mesh sections 260 wrap around the outer diameter of the lead body 205 when the lead is inserted through an introducer (not explicitly shown) during implantation. Therefore, the diameter of the introducer required to insert the lead into the pericardial space during implantation generally depends upon the width (i.e. length of the mesh section transverse to the lead body) and thickness and flexibility of the mesh.

One of skill in the art will appreciate however, that for a given surface area, the length verses the width of the mesh will have numerous variations that may be applied without further increasing the maximum outer diameter of the lead when the mesh sections are wrapped around the lead body during implantation. One of skill in the art will appreciate therefore, that the present invention is not limited to passive fixation mesh sections having a particular surface area or shape. Rather, the surface area and shape of the mesh sections may be varied to provide a desired level of fixation while maintaining a maximum outer diameter for insertion through a desired size introducer.

Figure 6:
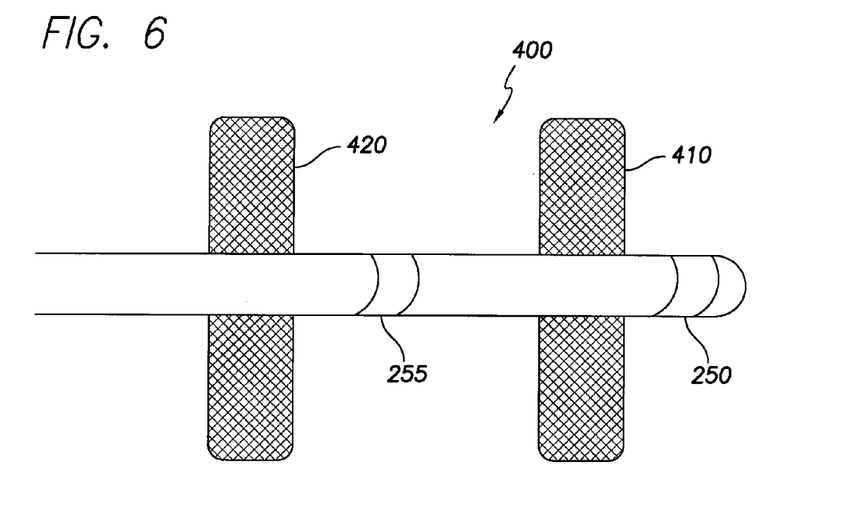
FIG. 6 is a top view of an epicardial lead having a first passive fixation mechanism between a distal electrode and a proximal electrode and a second passive fixation mechanism proximal of the proximal electrode in accordance with one embodiment of the present invention.

One of skill in the art will further appreciate that the present invention is not limited to two mesh sections integrated symmetrically between the distal tip electrode and proximal ring electrode. For example, FIG. 6 is a plan view of an epicardial lead 400 having a passive fixation mechanism that includes a first substantially symmetric mesh section 410 coupled to the lead body between the distal ring electrode 250 and a proximal ring electrode 255 and a second substantially symmetric mesh section 420 proximal of the ring electrode 255.

Figure 7:
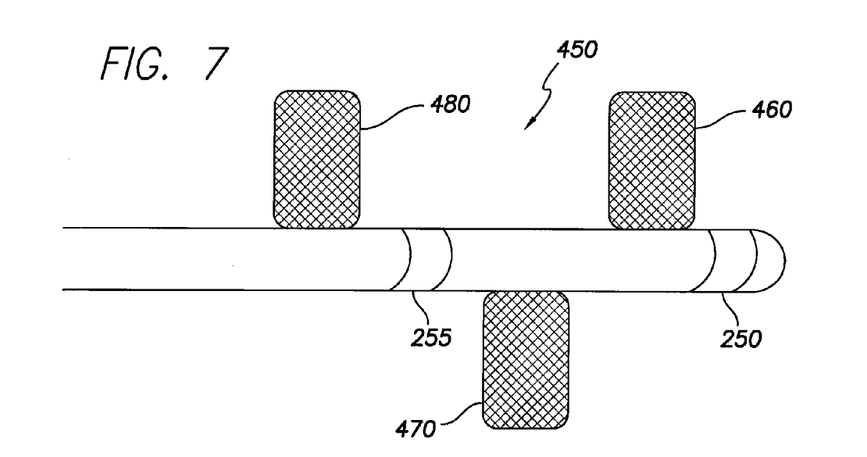
FIG. 7 is a top view of another epicardial lead having passive fixation mesh section on opposing sides of the lead body in accordance with one embodiment of the present invention.

Alternatively, FIG. 7 is a plan view of an epicardial lead 450 having a passive fixation mechanism that includes a first passive fixation mesh section 460 between the distal ring electrode 250 and the proximal ring electrode 255 and a second mesh section 470 between the first mesh section 460 and the proximal ring electrode 255. In this embodiment the first and section mesh sections are couple to opposite sides of the longitudinal axis of the lead body.

The passive fixation mechanism in this embodiment further includes a third mesh section 480 proximal off the proximal ring electrode 255. The separation of the mesh sections in this embodiment provides for increased mesh section surface area and fixation of the lead at multiple locations without significantly impacting the diameter of the introducer needed to implant the lead.

Furthermore, the passive fixation mechanism in one embodiment may include an electrode 250 integrated underneath a passive fixation mesh section 530 (see FIG. 8) to further stabilize the electrode. In this embodiment, electrode 250 may comprise a directional electrode that is biased against the heart surface for directing the electrical pathway toward the epicardial surface.

One of skill in the art will appreciate therefore that the present invention is not limited to the illustrated mesh section configurations. Rather, the passive fixation mesh sections of the present invention may be integrated in various configurations relative to the lead electrodes while still providing stable lead performance.

Furthermore, the passive fixation mechanism in another embodiment may include an absorbable mesh weave that is surrounded, at least in part, with a permanent edging material, such as silicone or other biocompatible materials that do not absorb into the body. In this embodiment the absorbable mesh weave provides acute fixation of the lead onto the epicardial surface but is absorbed by the body over a predetermined period of time. In this embodiment, fibrotic growth around the body of the lead and the permanent perimeter edging of the mesh section then provide chronic lead fixation and stability.

In one embodiment the absorbable mesh weave may be formed from a co-polymer such as, for example, lactide glycolide or other absorbable materials. In this embodiment the composition of the polymer material may be varied to control the time required for the absorbable mesh weave to absorb into the body. The absorption time can therefore be optimized to allow adequate time for tissue overgrowth on the permanent perimeter edging of the mesh sections and lead body to provide chronic fixation of the lead. An absorbable mesh section with a permanent perimeter is advantageous if the lead needs to be removed post implant because the fibrotic sheath which encapsulates the lead and mesh perimeter in the long term is more readily removed than tissue over growth within the mesh weave.

However, it typically requires between 1 to 24 hours for sufficient tissue overgrowth on the passive fixation mesh sections to fixate the lead in place, making it difficult to determine whether the lead will remain affix to the location at which it is implanted. Therefore, another embodiment of the present invention includes a second fixation mechanism, such as, for example, an inflatable member or balloon, coupled to the distal section of the lead body.

Figure 8:
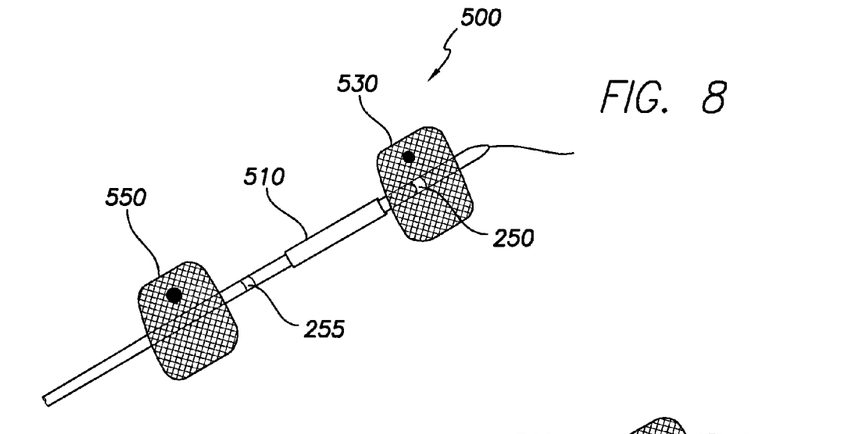
FIG. 8 is a perspective view of an epicardial lead having an inflatable member proximal of a distal electrode in accordance with one embodiment of the present invention.
Figure 9:
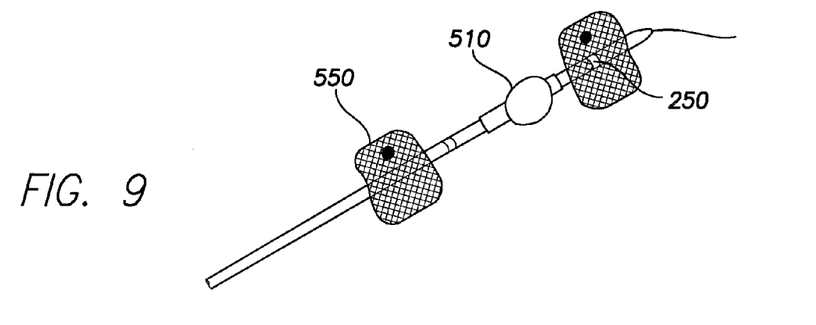
FIG. 9 is a perspective view of the epicardial lead of FIG. 8 having the inflatable member inflated in accordance with one embodiment of the present invention.

In this embodiment, an inflatable member 510, shown deflated in FIG. 8 and inflated in FIG. 9, is formed proximal of the distal electrode 250 and a first passive fixation mesh section 530. In a bipolar configuration, the lead 500 includes a proximal ring electrode 255 proximal of the inflatable member 510. The lead may further include one or more additional passive fixation mesh sections 550 proximal of the inflatable member 510.

In this embodiment the inflatable member 510 is inflated during implant to provide the necessary lead fixation and stability until the tissue over growth on the meshes becomes effective. One of skill in the art will appreciate that the inflatable member 510 can be shaped in various forms to improve the stability of the lead. However, in one embodiment a surface of the distal electrode 250 is coated, in part, with a suitable non-conductive coating to form a directional electrode.

In this embodiment the inflatable member 510 is positioned on the same side of the lead body as the non-conductive surface of the directional distal electrode 250. When inflated, the balloon tends to bias the lead body so that the conductive surface the distal electrode is fixated against the heart surface targeted for stimulation.

The inflatable member 510 may be formed of compliant or non-compliant biocompatible polymer materials such as for example, silicon, polyurethane, or other biocompatible materials known in the art. The expandable balloon may remain implanted indefinitely or may be formed, at least partially, of resorbable or biodegradable material that resorbs or undergoes biodegradation over time, such as polylactic acid, proteins/amino acid polymers, polyhydroxycarboxyl acids and/or carbohydrate polymers or the like. Alternatively, the inflatable member may be constructed of a material that is permeable or that has micro-pores to allow the fluid from within the inflatable member to slowly seep to the exterior of the balloon.

Figure 10:
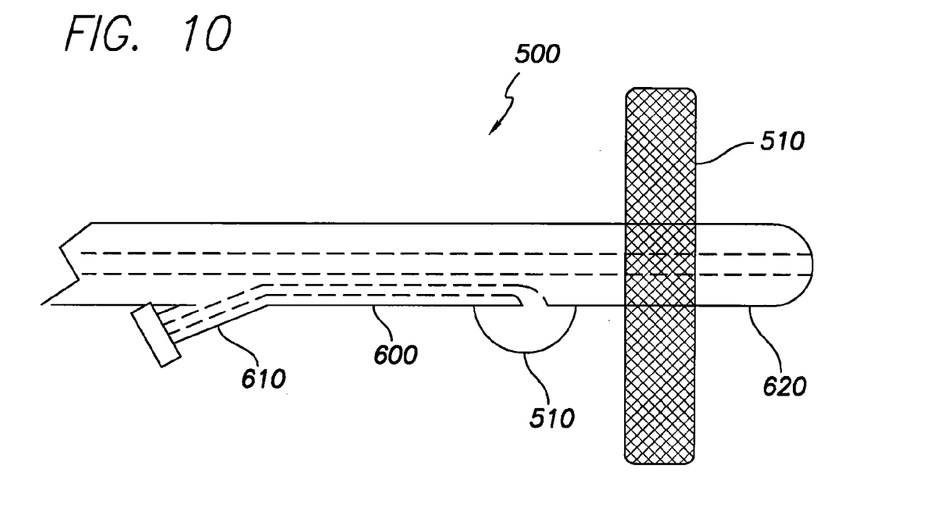
FIG. 10 is a cross section view of the epicardial lead of FIG. 9 illustrating an inflation lumen coupled between the inflatable member and a side arm in accordance with one embodiment of the present invention.
Figure 11:
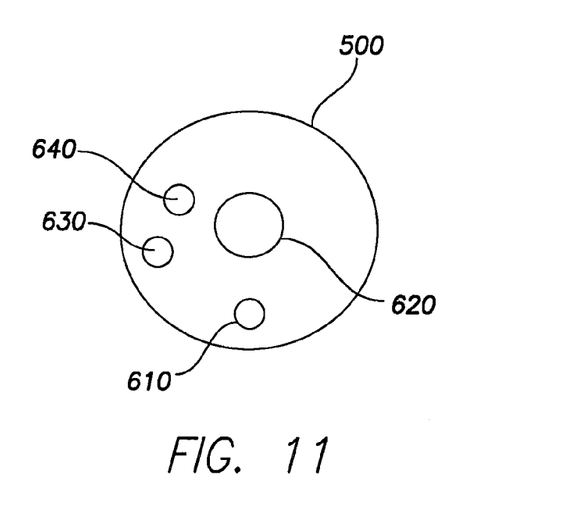
FIG. 11 is a cross section view of the epicardial lead of FIG. 8 illustrating the one or more lumen that extend down the longitudinal axis of the lead body in accordance with one embodiment of the present invention.

An inflation lumen 600, as shown in the cross sections of FIG. 10 and FIG. 11 extends along the body with one or more additional lumens 620, 630 and 640 which, in one embodiment, receive the center electrical conductor coupled to the distal electrode and redundant conductive cables which are coupled to the proximal electrode. In this embodiment the inflation lumen 600 is coupled between the inflatable member 510 at its distal opening and a side arm 610.

In one embodiment a syringe or other inflation source may be coupled to the side arm 610 to inject air, $CO_2$, a saline solution or other fluids into the inflation lumen 600 to expand the inflatable member 510 to a size that provides enough pressure between the pericardial sac and epicardial surface to effectively fixate the lead in place. Inflatable member may be fully or partially deflated by withdrawing fluid via the inflation lumen 600 so that the epicardial lead may be re-positioned, or withdrawn from the pericardial space.

It is often difficult to determine the location and orientation of the distal end of the epicardial lead during thoroscopic implantation and to determine the direction to steer it to get to a desired location. To accomplish catheter steering, a fluoroscope is typically utilized to provide real time in vivo viewing of the distal end of the epicardial lead location and orientation.

Figure 12:
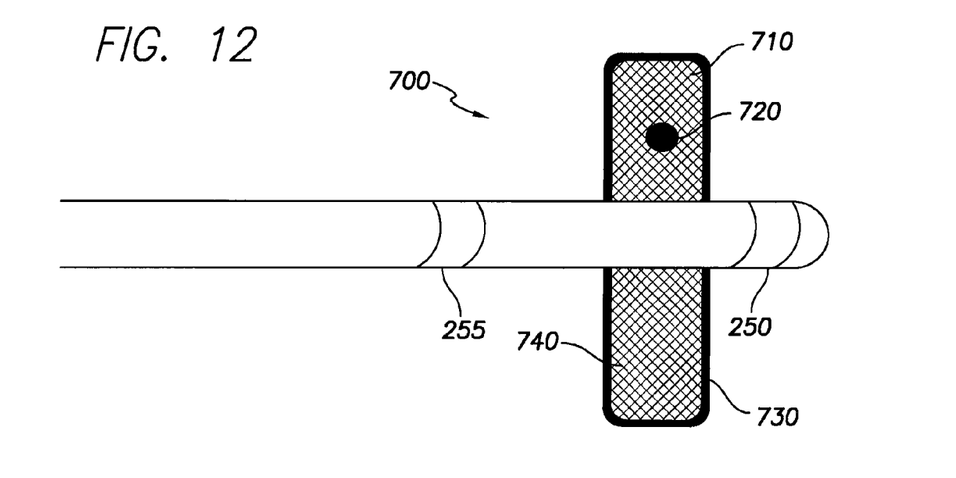
FIG. 12 is a top view of an epicardial lead having one or more passive fixation mesh sections and a fluoroscopic marker disposed on at least one of the mesh sections in accordance with one embodiment of the present invention.

Therefore, referring to the plan view of FIG. 12, an epicardial lead 700 in accordance with another embodiment of the present invention includes one or more passive fixation mesh sections 710 that include one or more fluoroscopic markers 720 disposed on the mesh sections to provide enhanced fluoroscopic visibility of the distal end of the lead during thoracoscopy implantation. The fluoroscopic marker 720 can be made of a material, like tungsten or barium sulfate, or a fluoro-opaque wire like platinum or gold.

In addition, the fluoroscopic marker can take any of a variety of shapes and sizes. In one embodiment a fluoroscopic identification maker may be formed in a ring 730 around the edges of one or more of the passive fixation mesh sections 710 and 740. The fluoroscopic maker around the edges of the mesh sections provide mechanical stability to ensure the meshes sections remain extended when inserted into the pericardial sac while providing visible feedback information to the physician regarding the position of the mesh sections.

Figure 13:
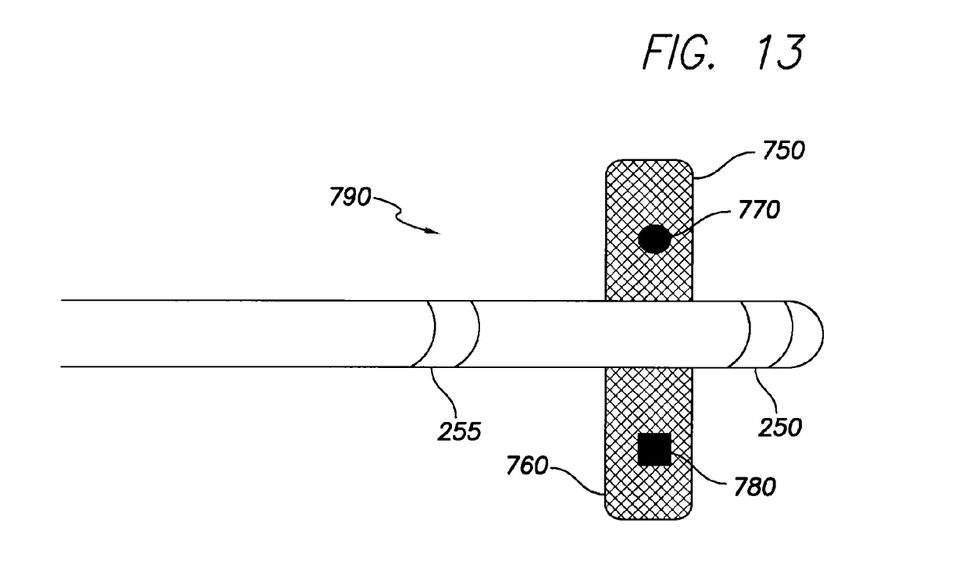
FIG. 13 is a top view of an epicardial lead having passive fixation mesh sections coupled on opposing sides of the longitudinal axis of the lead body and distinctive fluoroscopic markers disposed on the opposing mesh sections in accordance with one embodiment of the present invention.

Further, in another embodiment, distinctive fluoroscopic markers 770 and 780, having different sizes and or shapes, are integrated onto opposing passive fixation mesh sections 750 and 760 respectively as illustrated in FIG. 13. The distinctive fluoroscopic markers 770 and 780 provide enhanced fluoroscopically visible information to the physician regarding the location and orientation of the distal end of the lead including the lead electrodes. Knowing the orientation of the lead electrodes is especially advantageous when using a direction electrode that provides directed stimulation in a targeted direction.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. An implantable lead system, comprising:
   an elongated lead body defining a longitudinal axis and comprising an electrical conductor extending between a distal end of the lead body and a proximal end of the lead body;
   an electrode mounted on the distal end of the lead body, the electrode being coupled to the electrical conductor;
   one or more passive fixation mesh sections coupled to the lead that encourages tissue over growth and is adapted to transition between a collapsed state wherein it assumes a non-planar form allowing it to at least partially wrapped around the lead body and an extended state wherein it projects outward from the lead body; and
   an edge formed of silicone and secured to the mesh sections only around a perimeter of the mesh sections.

2. The implantable lead system of claim 1 further comprising a fluoroscopic marker disposed on one of the one or more passive fixation mesh sections.

3. The implantable lead system of claim 1 wherein the one or more passive fixation mesh sections comprise a first passive fixation mesh section coupled to a first side of the longitudinal axis of the lead body and a second passive fixation mesh section separate from the first passive fixation mesh section and coupled to an opposing side of the longitudinal axis of the lead body from the first mesh section.

4. The implantable lead system of claim 1 wherein the edge is impregnated with a fluoroscopically visible material to visualize the perimeters of the one or more mesh sections under fluoroscopy.

5. The implantable lead system of claim 1 wherein the one or more mesh sections comprise an absorbable mesh weave and the edge comprises a permanent biocompatible material.

6. An implantable lead system, comprising:
   an elongated lead body defining a longitudinal axis and comprising an electrical conductor extending between a distal end of the lead body and a proximal end of the lead body;
   an electrode mounted on the distal end of the lead body, the electrode being coupled to the electrical conductor;
   a first passive fixation mesh section coupled to a first side of the longitudinal axis of the lead body and a second passive fixation mesh section separate from the first passive fixation mesh section and coupled to an opposing side of the longitudinal axis of the lead body from the first mesh section, each of the mesh sections adapted to transition between a collapsed state wherein it is at least partially wrapped around the lead body and an extended state wherein it projects outward from the lead body; and
   a first fluoroscopic marker having a first shape disposed on the first passive fixation mesh section and a second fluoroscopic marker having a second shape different from the first shape and disposed on the second passive fixation mesh section.

7. The implantable lead system of claim 1 further wherein the electrode comprises a directional electrode having an insulating material applied to a portion of a surface of the electrode.

8. The implantable lead system of claim 1 further comprising a proximal connector coupled to the electrical conductor, wherein the proximal connector couples the electrode with an electrical stimulation device.

9. The implantable lead system of claim 1 further comprising a tubular insulating sheath overlying the conductor and having an outer peripheral surface of revolution defined by a radius originating at the longitudinal axis.

10. The implantable lead system of claim 1 further comprising an inflatable member proximal of said electrode, wherein the inflatable member is adapted to passively fixate the lead in place prior to tissue overgrowth on the one or more passive fixation mesh sections.

11. The implantable lead system of claim 10 further comprising an inflation lumen coupled between the inflatable member and a side arm so that an inflation material can be injected through said inflation lumen to inflated said inflatable member.

12. The implantable lead system of claim 10 wherein the inflatable member consists entirely of a biodegradable material that resorbs or undergoes biodegradation over time.

13. The implantable lead system of claim 10 wherein the inflatable member comprises a permeable material to release an inflation material within the inflatable member to the exterior of the inflatable member over time.

14. The implantable lead system of claim 1 wherein the one or more passive fixation mesh sections comprise polyester passive fixation mesh sections.

15. The implantable lead system of claim 1 further comprising a center lumen proceeding entirely along said longitudinal axis forming a channel adapted to engage a stylet for stylet placement of the lead.

16. An implantable lead system, comprising:
   an elongated lead body defining a longitudinal axis and comprising an electrical conductor extending between a distal end of the lead body and a proximal end of the lead body;
   an electrode mounted on the distal end of the lead body, the electrode being coupled to the electrical conductor;
   one or more passive fixation mesh sections coupled to the lead body that encourages tissue over growth and is adapted to transition between a collapsed state wherein it assumes a non-planar form allowing it to at least partially wrapped around the lead body and an extended state wherein it projects outward from the lead body;

an edge formed of silicone and secured to the mesh sections only around a perimeter of the mesh sections; and an introducer adapted to receive the lead body when the one or more passive fixation mesh sections are in a collapsed state and to introduce the elongated lead body into a patient's pericardial sac.

17. The implantable lead system of claim 16 further comprising a fluoroscopic marker disposed on one of the one or more passive fixation mesh sections.

18. The implantable lead system of claim 16 wherein the edge is impregnated with a fluoroscopically visible material to visualize the perimeters of the one or more mesh sections under fluoroscopy.

19. The implantable lead system of claim 16 wherein the one or more mesh sections comprise an absorbable mesh weave and the edge comprises a permanent biocompatible material.

20. The implantable lead system of claim 16 further wherein the electrode comprises a directional electrode having an insulating material applied to a portion of a surface of the electrode.

21. The implantable lead system of claim 16 further comprising an inflatable member proximal of said electrode, wherein the inflatable member is adapted to passively fixate the lead in place prior to tissue overgrowth on the one or more passive fixation mesh sections.

22. The implantable lead system of claim 21 further comprising an inflation lumen coupled between the inflatable member and a side arm so that an inflation material can be injected through said inflation lumen to inflated said inflatable member.

23. The implantable lead system of claim 21 wherein the inflatable member consists entirely of a biodegradable material that resorbs or undergoes biodegradation over time.

24. The implantable lead system of claim 21 wherein the inflatable member comprises a permeable material to release an inflation material within the inflatable member to exterior of the inflatable member over time.

25. The implantable lead system of claim 16 wherein the one or more passive fixation mesh sections comprise polyester passive fixation mesh sections.

26. An implantable lead system, comprising:

an elongated lead body defining a longitudinal axis, the lead body including an electrical conductor extending between a distal end of the lead body and a proximal end of the lead body;

an electrode mounted on the distal end of the lead body, the electrode being coupled to the electrical conductor;

a first passive fixation mesh section coupled to the lead body;

a second passive fixation mesh section, separate from the first passive fixation mesh section, and coupled to an opposing side of the longitudinal axis of the lead body from the first passive mesh section; and an edge around a perimeter of at least one of the mesh sections that is secured to the mesh sections only at a perimeter of the mesh section.

27. The implantable lead system of claim 26 wherein the edge is impregnated with a fluoroscopically visible material to visualize the perimeters of the one or more mesh sections under fluoroscopy.

28. The implantable lead system of claim 26 wherein the one or more mesh sections comprise an absorbable mesh weave and wherein the edge comprises a permanent biocompatible material.

29. The implantable lead system of claim 26 wherein the second passive fixation mesh section is proximate the first passive fixation mesh section.

30. The implantable lead system of claim 27 further comprising a third passive fixation mesh section, separate from and proximate the first passive fixation mesh section and the second passive fixation mesh section.

* * * * *